US00PP37480P2

(12) United States Plant Patent
Yamada et al.

(10) Patent No.: US PP37,480 P2
(45) Date of Patent: Jun. 23, 2026

(54) ***MANDEVILLA* PLANT NAMED 'Sunpa 2361'**

(50) Latin Name: *Mandevilla hybrida*
Varietal Denomination: Sunpa 2361

(71) Applicants: Masahiro Yamada, Higashiomi (JP); Tomoya Misato, Higashiomi (JP)

(72) Inventors: Masahiro Yamada, Higashiomi (JP); Tomoya Misato, Higashiomi (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 19/003,606

(22) Filed: Dec. 27, 2024

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
CPC . A01H 5/02; A01H 5/00; A01H 6/088; A01H 6/08
See application file for complete search history.

(56) References Cited

PUBLICATIONS

Beytes et al. 2024 Growers Talk California Spring Trials Day 2: Green Fuse Botanicals & Santa Barbara Polo Club (9 Companies), retrieved on Mar. 18, 2025 at https://www.growertalks.com/Newsletters/View/?article=4499, 20 pp. (Year: 2024).*
BFG Sun-Fire Nurseries 2024 Program, retrieved on Mar. 18, 2025 at https://www.bfgsupply.com/media/9000/2024-sunfire-product-program.pdf, 9 pp. (Year: 2024).*
Greenhouse Management 2024 California Spring Trials Preview: Suntory Flowers, retrieved on Mar. 18, 2025 at https://www.greenhousemag.com/page/suntory-flowers-california-spring-trials/, 12 pp. (Year: 2024).*
Suntory Flowers 2025 Catalog, retrieved on Mar. 18, 2025 at https://suntoryflowers.com/wp-content/uploads/2024/02/2025-Suntory-Flowers-Catalog.pdf, pp. 1-3, 14, 64. (Year: 2025).*

* cited by examiner

*Primary Examiner* — June Hwu
(74) *Attorney, Agent, or Firm* — C. Anne Whealy

(57) ABSTRACT

A new and distinct cultivar of *Mandevilla* plant named 'Sunpa 2361', characterized by its semi-climbing plant habit; vigorous growth plant habit; freely branching habit; freely flowering habit; long flowering period; large red-colored flowers; and good garden performance.

2 Drawing Sheets

Figure 1:
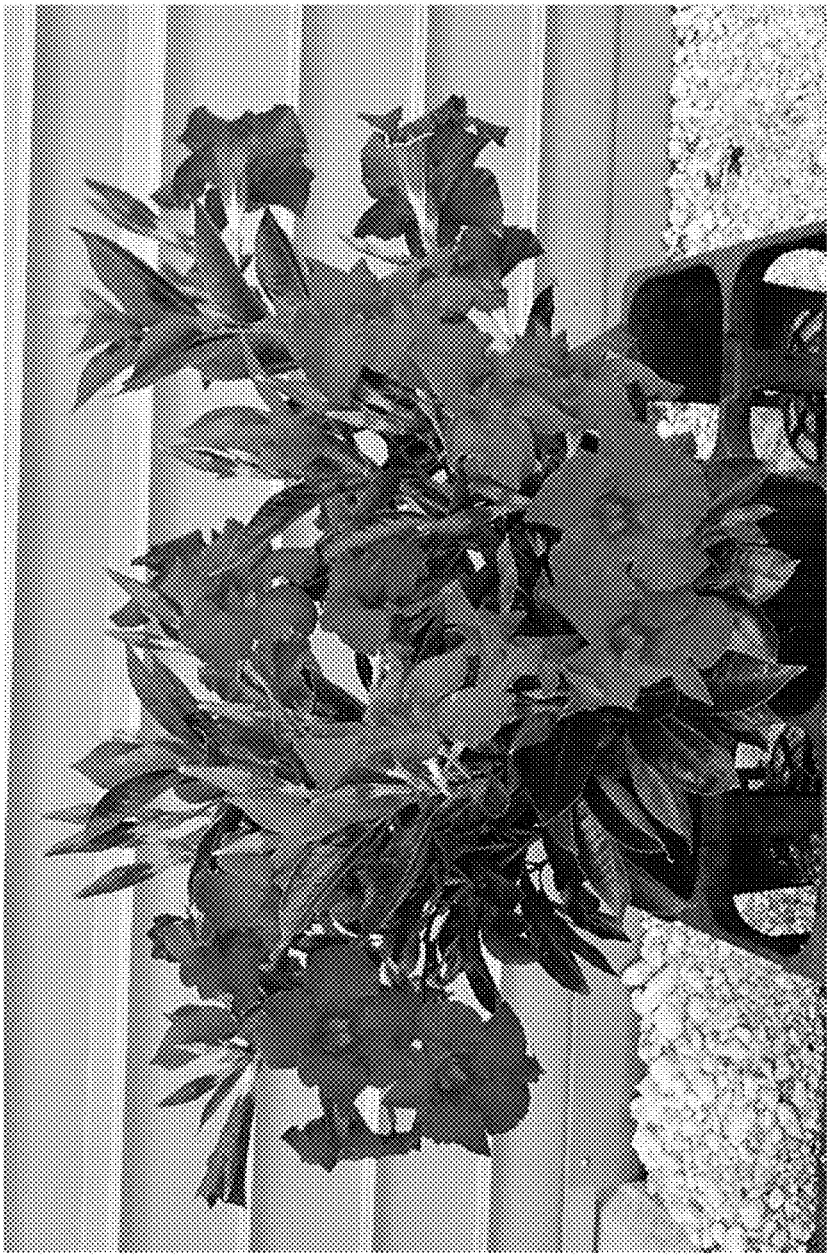

Botanical designation: *Mandevilla hybrida.*
Cultivar denomination: 'SUNPA 2361'.

BACKGROUND OF THE INVENTION

The present invention relates to a new and distinct cultivar of *Mandevilla* plant, botanically known as *Mandevilla hybrida* and hereinafter referred to by the name 'Sunpa 2361'.

The new *Mandevilla* plant is a product of a planned breeding program conducted by the Inventors in Higashiomi, Shiga, Japan. The objective of the breeding program is to develop new compact *Mandevilla* plants with a semi-climbing plant habit and numerous large red-colored flowers.

The new *Mandevilla* plant originated from a cross-pollination by the Inventors in May, 2016 in Higashiomi, Shiga, Japan of a proprietary selection of *Mandevilla hybrida* identified as code number MY15042-23, not patented, as the female, or seed, parent with a proprietary selection of *Mandevilla hybrida* identified as code number 14M532-1, not patented, as the male, or pollen, parent. The new *Mandevilla* plant was discovered and selected by the Inventors as a single flowering plant from within the progeny of the stated cross-pollination grown in a controlled greenhouse environment in Higashiomi, Shiga, Japan in September, 2019.

Asexual reproduction of the new *Mandevilla* plant by terminal vegetative cuttings in Higashiomi, Shiga, Japan since March, 2020 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 2361'. These characteristics in combination distinguish 'Sunpa 2361' as a new and distinct *Mandevilla* plant:

1. Semi-climbing plant habit.
2. Vigorous growth habit.
3. Freely branching habit.
4. Freely flowering habit.
5. Long flowering period.
6. Large red-colored flowers.
7. Good garden performance.

Plants of the new *Mandevilla* can be compared to plants of the female selection parent. Plants of the new *Mandevilla* differ primarily from plants of the female parent selection in plant habit as plants of the new *Mandevilla* are semi-climbing types whereas plants of the female parent selection are climbing types. In addition, plants of the new *Mandevilla* have much larger flowers than plants of the female parent selection.

Plants of the new *Mandevilla* can be compared to plants of the male selection parent. Plants of the new *Mandevilla* differ primarily from plants of the male parent selection in plant habit as plants of the new *Mandevilla* are semi-climbing types whereas plants of the male parent selection are non-climbing types. In addition, plants of the new *Mandevilla* have larger flowers than plants of the male parent selection.

Plants of the new *Mandevilla* can be compared to plants of the *Mandevilla* x *amabilis* 'Sunparacore', disclosed in U.S. Plant Pat. No. 23,959. In side-by-side comparisons, plants of the new *Mandevilla* differ from plants of 'Sunparacore' in the following characteristics:

1. Plants of the new *Mandevilla* are semi-climbing types whereas plants of 'Sunparacore' are non-climbing types.
2. Leaf arrangement of plants of the new *Mandevilla* is decussate whereas leaf arrangement of plants of 'Sunparacore' is opposite.
3. Plants of the new *Mandevilla* have larger leaves than plants of 'Sunparacore'.
4. Plants of the new *Mandevilla* have larger flowers than plants of 'Sunparacore'.
5. Flower petals of plants of the new *Mandevilla* are free and not imbricate whereas flower petals of plants of 'Sunparacore' are imbricate.
6. Flower petals of plants of the new *Mandevilla* are lighter red in color than flower petals of plants of 'Sunparacore'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'Sunpa 2361' grown in a container.

Figure 2:
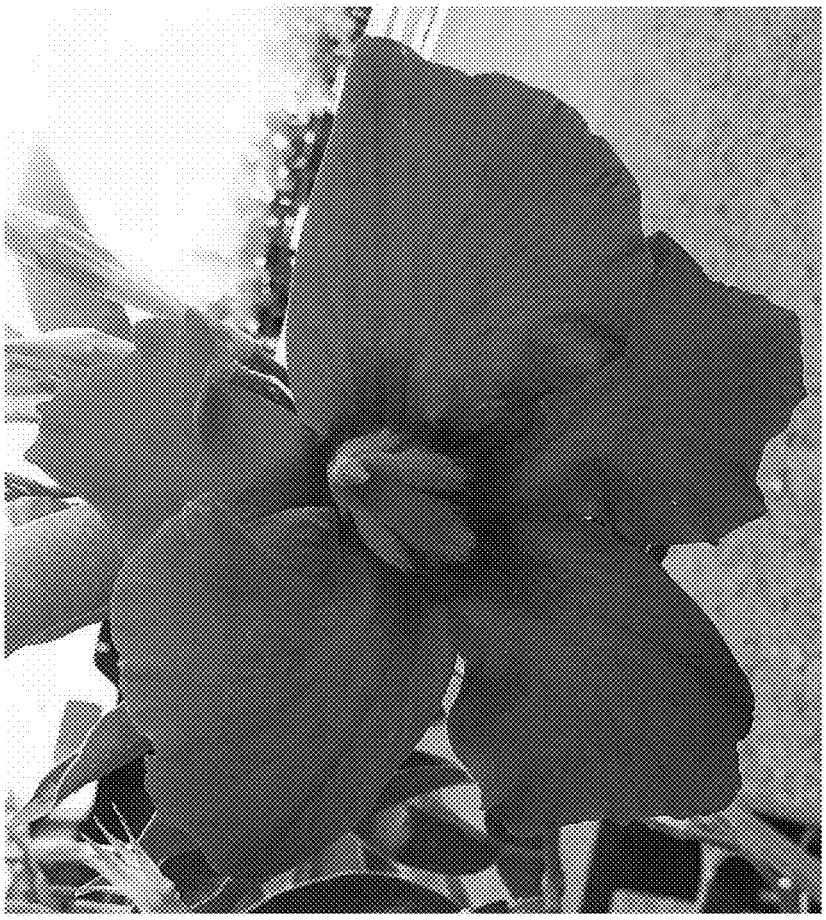

The photograph on the second sheet (FIG. 2) is a close-up view of a typical flower and flower buds of 'Sunpa 2361'.

DETAILED BOTANICAL DESCRIPTION

The aforementioned photographs and following observations, measurements and values describe plants grown during the late summer/early autumn in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months from planting rooted young plants when the photographs and the detailed description were taken. In the following description, color references are made to The Royal Horticultural Society Colour Chart, 2015 Edition, except where general terms of ordinary dictionary significance are used.

Botanical classification:

*Mandevilla hybrida* 'Sunpa 2361'.

Parentage:

*Female, or seed, parent*.—Proprietary selection of *Mandevilla hybrida* identified as code number MY15042-23, not patented.

*Male, or pollen, parent*.—Proprietary selection of *Mandevilla hybrida* identified as code number 14M532-1, not patented.

Propagation:

*Type*.—By terminal vegetative cuttings.

*Time to initiate roots, summer and winter*.—About two weeks at temperatures about 23° C. to 25° C.

*Time to produce a rooted young plant, summer and winter*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Semi-climbing plant habit; vigorous growth habit; freely basal branching habit; suitable for hanging baskets and garden plantings.

*Plant height*.—About 125 cm.

*Plant diameter*.—About 66 cm.

*Lateral branch description*.—Length: About 125 cm. Diameter: About 4.2 mm. Internode length: About 2.8 cm. Strength: Strong, flexible. Aspect: Mostly upright. Texture: Smooth, glabrous. Color, developing: Close to 144B. Color, fully developed: Close to 177B.

Leaf description:

*Arrangement and quantity*.—Decussate, simple; dense, about 38 leaves per lateral branch.

*Length*.—About 8.6 cm.

*Width*.—About 4.9 cm.

*Shape*.—Oblong; incurving.

*Apex*.—Acuminate.

*Base*.—Acute.

*Margin*.—Entire; not undulate to slightly undulate.

*Texture and luster, upper and lower surfaces*.—Smooth, glabrous; moderately glossy.

*Venation pattern*.—Pinnate, reticulate.

*Color*.—Developing leaves, upper surface: Close to 143A. Developing leaves, lower surface: Close to 143C. Fully expanded leaves, upper surface: Close to NN137A; venation, close to 144B. Fully expanded leaves, lower surface: Close to 138A; venation, close to 144C.

*Petioles*.—Length: About 1.5 cm. Diameter: About 1.8 mm. Texture, upper and lower surfaces: Smooth, glabrous. Color, upper and lower surfaces: Close to 144B.

Flower description:

*Flower type and habit*.—Single-type flowers; flowers face mostly outwardly; freely flowering habit with about three flowers per axil and about 66 developing and open flowers at one time during the flowering season.

*Natural flowering season*.—Plants begin flowering about six weeks after planting rooted young plants;

long flowering period, plants flower continuously from summer until late autumn in Japan.

*Flower longevity on the plant*.—About seven to ten days; flowers not persistent.

*Fragrance*.—None detected.

*Flower buds*.—Height: About 6.7 cm. Diameter: About 1.2 cm. Shape: Rhombic. Color: Close to 53A.

*Flowers*.—Appearance: Single-type, five petals in a single whorl; flowers salverform with campanulate throats. Diameter: About 8.4 cm. Depth (length): About 6.3 cm.

*Corolla*.—Quantity and arrangement: Five petals fused towards the base into an elongated throat and tube; petal lobes free and not imbricate. Petal lobe length: About 4 cm. Petal lobe width: About 3.7 cm. Throat diameter, distally: About 1.8 cm. Throat diameter, proximally: About 6.8 mm. Throat length: About 2.9 cm. Tube length: About 1.7 cm. Tube diameter, proximally: About 3.5 mm. Petal lobe shape: Spatulate, strongly asymmetrical. Petal lobe apex: Acute. Petal lobe margin: Entire; moderately undulate and moderately recurving. Petal lobe texture and luster, upper and lower surfaces: Smooth, glabrous; matte. Throat texture: Smooth, glabrous. Tube texture: Smooth, glabrous. Color: Petal lobe, when opening and fully opened, upper surface: Close to N45A and towards the throat, close to 53A; venation, similar to lamina colors; colors do not change with subsequent development. Petal lobe, when opening and fully opened, lower surface: Close to N45B and towards the tube, close to N45A; venation, similar to lamina colors; colors do not change with subsequent development. Throat, inner surface: Distally, close to 53A and 170A, and proximally, close to 169A; venation, close to 53A. Throat, outer surface: Distally, close to 53C, and proximally, close to 53C and 145C; venation, close to 145B. Tube: Close to 145C, 53C and 63A; venation, similar to lamina colors.

*Calyx*.—Quantity and arrangement: Five sepals arranged in a single whorl, fused at the base into a tube; calyx, star-shaped. Sepal length: About 7.7 mm. Sepal width: About 2.8 mm. Sepal shape: Lanceolate. Sepal apex: Acuminate. Sepal margin: Entire. Sepal texture, upper and lower surfaces: Smooth, glabrous. Sepal color, upper surface: Distally, close to 58A, and proximally, close to 144C. Sepal color, lower surface: Distally, close to 58A, and proximally, close to 144B.

*Peduncles*.—Length: About 2.2 cm. Diameter: About 2.3 mm. Texture: Smooth, glabrous. Aspect: Upright to outwardly. Color: Close to 144A.

*Pedicels*.—Length: About 1.7 cm. Diameter: About 2.4 mm. Texture: Smooth, glabrous. Aspect: Upright to outwardly. Color: Close to 144B.

*Reproductive organs*.—Stamens: Quantity: Five. Anther size: About 1.3 mm by 4.5 mm. Anther shape: Lanceolate. Anther color: Close to 10B. Amount of pollen: Sparse. Pollen color: Close to 10B. Pistils: Quantity: Typically one. Pistil length: About 2.5 cm. Style color: Close to 145C. Stigma shape: Conical. Stigma color: Close to 151B. Ovary color: Close to 145A.

*Seeds and fruits*.—To date, seed and fruit development have not been observed on plants of the new *Mandevilla*.

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C. and to be suitable for USDA Hardiness Zones 11 and 12.

It is claimed:

1. A new and distinct *Mandevilla* plant named 'Sunpa 2361' as herein illustrated and described.

* * * * *